United States Patent [19]

Frazier et al.

[11] Patent Number: 4,895,795

[45] Date of Patent: Jan. 23, 1990

[54] DETECTION AND DIFFERENTIATION OF COXIELLA BURNETII IN BIOLOGICAL FLUIDS

[75] Inventors: Marvin E. Frazier, Richland, Wash.; Louis P. Mallavia, Moscow, Id.; James E. Samuel, Pullman, Wash.; Oswald G. Baca, Albuquerque, N. Mex.

[73] Assignee: Battelle Development Corporation, Columbus, Ohio

[21] Appl. No.: 927,779

[22] Filed: Nov. 5, 1986

Related U.S. Application Data

[63] Continuation-in-part of Ser. No. 795,207, Nov. 5, 1985.

[51] Int. Cl.$^4$ .......................... C12Q 1/68; C12Q 1/04
[52] U.S. Cl. ......................................... 435/6; 435/34; 435/35; 435/172.3; 435/320; 436/63; 436/501; 536/27; 935/29; 935/78
[58] Field of Search ..................... 435/6, 34, 35, 172.3, 435/317; 436/63, 501; 536/27; 935/29, 78

[56] References Cited

U.S. PATENT DOCUMENTS

| | | | |
|---|---|---|---|
| 4,332,898 | 6/1982 | Reusser | 435/320 X |
| 4,358,535 | 11/1982 | Falkow et al. | 435/34 X |
| 4,563,419 | 1/1986 | Ranki et al. | 435/188 X |

OTHER PUBLICATIONS

O. G. Baca and D. Paretsky, "Q Fever and *Coxiella burnetii*: A Model for Host-Parasite Interactions", *Microbial Rev.* 47: 127-149, 1983.

R. A. Ormsbee, "Q Fever Rickettsia", in *Viral and Rickettsial Infections of Man*, 4th Ed., F. L. Horsfall, Jr. and I. Tamm (ed), J. B. Lippincott Co., PA, 1965, pp. 1144-1460.

M. G. Peacock et al., "Serological Evaluation of Q fever in Humans: Enhanced Phase I Titers of Immunoglobulins G and A are Diagnostic for Q Fever Endocarditis", *Infect. Immun.* 41:1089-1098, 1983.

W. P. G. Turck et al., "Chronic Q Fever", *Q. J. Med.* 45:193-217, 1976.

M. J. Tobin e al., "Q Fever Endocarditis", *Am. J. Med.* 72: 396-400, 1982.

A. O. Robson and C. D. G. L. Shimmin, "Chronic Q Fever-I. Clinical Aspects of a Patient with Endocarditis", *Br. Med. J.* 2: 980-983 1959.

M. G. P. Stoker and P. Fiset, "Phase Variation of the Nine Mile and Other Strains of Rickettsia Burnetii", *Can J. Microbiol.* 2:310-321, 1956.

J. E. Samuel et al., "Isolation and Characterization of a Plasmid from Phase I *Coxiella burnetii*", Infect. Immun. 41:488-493, 1983.

L. P. Mallavia et al., "*Coxiella burnetii* Plasmid DNA', in *Microbiology 1984*", L. Leive and D. Schlessinger (ed.), Amer. Soc. Microbiol., Washington, D.C., 1984, pp. 293-296.

J. E. Samuel et al., "Correlation of Plasmid Type and Disease Caused by *Coxiella burnetii*", *Infect. Immun.* 49:775-779, 1985.

J. J. Leary et al., "Rapid and Sensitive Colorimetric Method for Visualizing Biotin-Labeled DNA Probes Hybridized to DNA or RNA Immobilized on Nitrocellulose: Bio-Blots", *Proc. Natl. Acad. Sci. U.S.A.* 80:4045-4049, 1983.

*Primary Examiner*—Robert J. Warden
*Assistant Examiner*—Richard Wagner
*Attorney, Agent, or Firm*—Seed and Berry

[57] ABSTRACT

Methods for detecting the presence of *Coxiella burenetii* in biological samples, as well as a method for differentiating strains of *C. burnetii* that are capable of causing acute disease from those strains capable of causing chronic disease are disclosed. The methods generally comprise treating cells contained within the biological sample to expose cellular DNA, and hybridizing the cellular DNA (specifically rickettsial DNA) with a *C. burnetii*-specific labeled DNA probe. Radioisotope and biotin labels are preferred, allowing detection through autoradiography and colorimetric assays, respectively.

6 Claims, 4 Drawing Sheets

| QpHI | A' | B' | C' | D' | E' | F' | G' | H' | I' | J' |
|---|---|---|---|---|---|---|---|---|---|---|
| QpRS | A+B | C | D | | G | | F | F | g | E |

EcoRI FRAGMENT HOMOLOGIES BETWEEN QpHI AND QpRS

DETECTION AND DIFFERENTIATION OF COXIELLA BURNETII IN BIOLOGICAL FLUIDS

CROSS-REFERENCE TO RELATED APPLICATION

This application is a continuation-in-part of applicant's co-pending application Ser. No. 795,207, filed Nov. 5, 1985, which application is pending.

TECHNICAL FIELD

The present invention relates to a method for detecting *Coxiella burnetii* infection in humans and animals, and to a method for differentiating *C. burnetii* strains which cause acute Q fever from those capable of causing chronic infections (e.g., endocarditis, hepatitis or late-term abortions).

BACKGROUND ART

*Coxiella burnetii*, the causative agent of Q fever, is an obligate intracellular parasite which is generally transmitted from animals to humans. Domestic livestock serve as a reservoir for Q fever in most parts of the world, and usually presents as an inapparent infection; in sheep, however, it may lead to late-term abortion. In domestic animals (sheep, goats, cattle), the disease is shed and transmitted either by aerosol or through an intermediate vector (tick). Further, apparently healthy animals may contain enormous numbers of parasites in placental tissues. (Luoto & Huebner, *Public Health Rep.* 65:541-544, 1950).

Although Q fever may be transmitted to humans by ticks, it is usually contracted by inhalation of contaminated dusts and aerosols; contagion between humans is rare. *Coxiella burnetii* is known to infect many species of animals and birds (Babudieri, B., *Adv. Vet. Sci.* 5:81-154, 1959). Q fever is most common among slaughterhouse employees and farm workers who handle animals (domestic cattle, sheep and goats) or animal products (e.g., wool, hides) (Ormsbee, R. A., *Ann. Rev. Microbiol.* 23:275-292 (1962); Baca & Paretsky, *Microbiol. Rev.* 47:127-149, 1983).

The acute form of Q fever is rarely fatal to humans. The death rate has been estimated at less than 1% among Caucasians, and somewhat higher among indigenous people of equatorial Africa (Ormsbee, R. A., *Viral and Rickettsial Infections of Man;* 4th Ed., ed. F. L. Horsfall Jr. and I. Tamm, pp. 1144-1160, 1965, J. B. Lippincott Co., Penn.). The incubation period ranges from 1 to 3 weeks, and the disease normally presents as an acute febrile illness. Recovery generally occurs within 1 to 4 weeks, depending on the course of treatment. Occasionally, *C. burnetii* infection is manifested in other ways, including inapparent persistent infection, which can lead to endocarditis or other symptoms in man. The development of chronic endocarditis in humans has previously been thought to arise when a *C. burnetii* infection is superimposed on a pre-existing disease or deformity of the patient, rather than to a specific property of the pathogen (Peacock et al., *Infect. & Immun.* 41:1089-1098, 1983; Turck et al., *J. of Medicine* 178:193-217, 1976; Tobin et al., *Amer. J. of Med.* 72: 396-399, 1982; Robson et al., *British Med. J.* 2:980-983, 1959). Comparative analyses of infected sera and of the biological properties of microorganisms isolated from various sequelae of Q fever (acute infection, chronic endocarditis, abortion, etc.) have not indicated that specific *C. burnetii* variants produce a particular manifestation. Comparative analyses have, however, demonstrated antigenic variation in *C. burnetii* (Stoker, M. G. P. and P. Fiset, *Can. J. Microbiol.* 2:310-321, 1956). This antigenic phase variation is characterized primarily by the reactivity of different isolates with hyperimmune sera against phase I or phase II Nine Mile strain of *C. burnetii*. However, this phenotypic variation cannot be used to predict sequelae of *C. burnetii* infection.

Differentiation of Q fever from influenza, primary atypical pneumonia, bacterial pneumonia, or a number of other types of pneumonia and flu-like symptoms caused by a variety of etiological agents is a slow and difficult process. It is also difficult to differentiate *C. burnetti*-induced hepatitis from infectious or idiopathic hepatitis. Differentiation procedures presently used require isolation of *C. burnetii* from tissues or blood, and subsequent culture in embryonated eggs or in guinea pigs. An alternative method for differentiation requires demonstration of a significant rise in specific anti-*C. burnetii* antibody titer in successive serum samples. Isolation of *C. burnetii* is highly hazardous, and is inadvisable in the absence of adequate (P-3) isolation facilities. Even then, safety procedures must be rigidly followed to avoid contamination. In addition, confirmation of findings usually takes 2 to 3 weeks. Serological methods, while simpler and safer than culturing, also require considerable time (usually 3 weeks) to confirm the diagnosis, and are therefore of little use to a practicing physician, who usually prefers to start treatment within 24 hours. In addition to being costly and time-consuming, both techniques require highly specialized facilities, equipment, and reagents that are generally available only in special laboratories. Furthermore, serological diagnosis of chronic *Coxiella burnetii* infections would be difficult since the appropriate (pre-immune) serum sample necessary for a definitive diagnosis would not be available.

Due to these difficulties in diagnosis, it is hard to accurately estimate the prevalence of *C. burnetii* infection throughout the world. Furthermore, there has been no way to predict from the initial symptoms the result of the infection, i.e., whether it will result in a persistent infection, including hepatitis and/or chronic endocarditis, or an acute attack of Q fever.

There exists a need in the art, then, for a rapid, sensitive, and simple method for the detection of *C. burnetii* in biological samples. In addition, a method for distinguishing *C. burnetii* strains capable of causing chronic infection from those associated only with acute infection would be useful for determining optimal patient treatment. The present invention fulfills these needs and further provides other related advantages.

DISCLOSURE OF THE INVENTION

Briefly stated, the present invention discloses methods for detecting the presence of *Coxiella burnetii* in biological samples, comprising treating cells contained within the biological sample to expose cellular DNA; hybridizing the cellular DNA with a *C. burnetii*-specific labeled DNA probe; and detecting the hybridized, labeled DNA probe. It is also preferable to first immobilize the cells contained within the biological sample onto a solid support. For purposes of the present invention the terms "cellular DNA" are defined to include any and all DNA present within the cell, including the DNA of any infectious agent, such as rickettsial DNA, to which the probes will hybridize.

A variety of biological samples are suitable for use within the methods described herein, including samples of blood, urine or milk.

A related aspect of the present invention discloses a method for detecting the presence of strains of C. burnetii that are capable of causing chronic disease, comprising: (a) treating cells contained within a biological sample to expose cellular DNA; (b) hybridizing the cellular DNA with a labeled DNA probe containing DNA sequences that specifically recognize C. burnetii DNA of strains associated with the capacity to cause chronic disease; and (c) detecting the hybridized, labeled DNA probe and therefrom determining the presence of strains of C. burnetii capable of causing chronic disease.

A third aspect of the present invention discloses a method for differentiating strains of C. burnetii that are capable of causing acute disease from those capable of causing chronic disease, comprising (a) treating cells suspected of containing C. burnetii to expose cellular DNA; (b) hybridizing a portion of the cellular DNA with a C. burnetii-specific labeled DNA probe; (c) hybridizing another portion of the cellular DNA with a labeled DNA probe containing DNA sequences that specifically recognize C. burnetii DNA of strains associated with the capacity to cause chronic disease; and (d) detecting the hybridized, labeled DNA probes, and therefrom differentiating the strain of C. burnetii. Recombinant plasmids containing DNA sequences that specifically recognize C. burnetii DNA are also disclosed.

These and other aspects of the invention will become apparent upon reference to the following detailed description and attached drawings.

BEST MODE FOR CARRYING OUT THE INVENTION

As noted above, current diagnosis of C. burnetii infection is a complicated, time-consuming, and hazardous procedure. Isolation of C. burnetii requires specialized and expensive culture medium, and should be performed in P-3 isolation facilities. While serologic detection is simpler and safer, confirmatory diagnosis of C. burnetii infection may take weeks. Currently, there is no way to predict whether C. burnetii infection will result in chronic or acute disease.

Recently, examination of the virulence of a variety of C. burnetii strains resulted in the detection of a plasmid in the Nine Mile strain of C. burnetii (Samuel et al., Infect. & Immun. 41:488–493, 1983; Mallavia et al., in: Microbiology, Amer. Soc. for Microbiol., Wash., DC, pp. 293–296, 1984). Prior studies of the role of plasmids in 10 other organisms indicated that plasmids may encode virulence determinants. Efforts leading up to the present invention have shown that the C. burnetii plasmid designated QpH1 is rickettsia-specific, with a molecular mass of $2.4 \times 10^6$ daltons, and that it is present in low copy number. Plasmid DNA, which was present in both phase I and phase II variants, did not appear to be overtly involved in phase variation, however, and functions of the plasmid DNA remained cryptic (Samuel et al., Infect. & Immun. 49:775–779, 1985).

Figure 1:
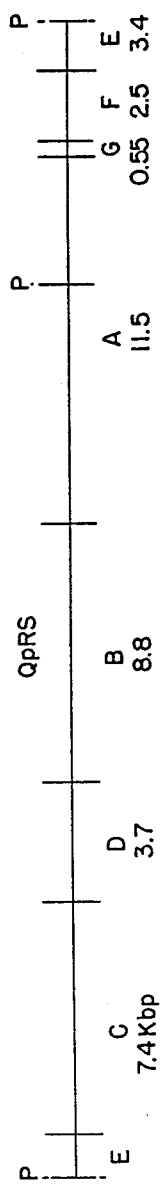
FIG. 1 depicts a comparison of Eco RI restriction fragments of C. burnetii plasmids QpH1 and QpRS.
Figure 1:
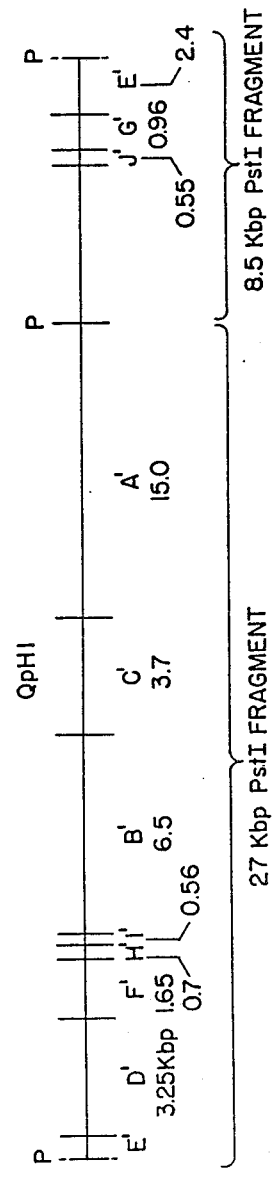
Figure 2:
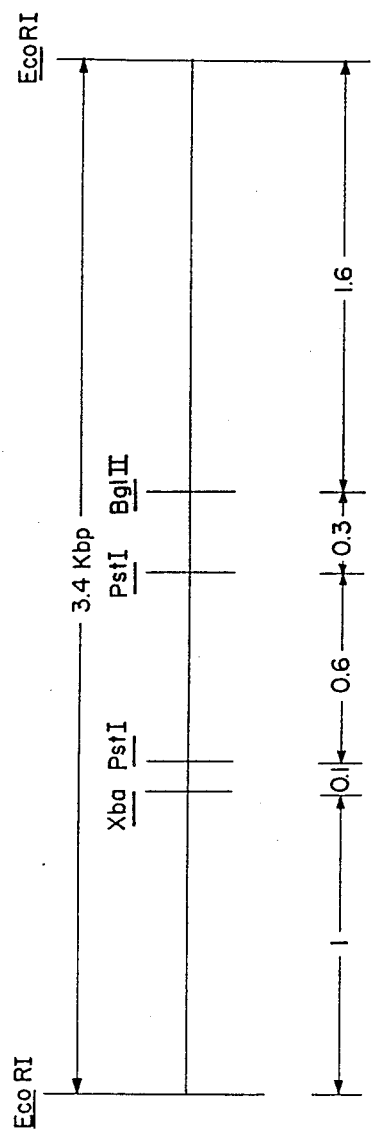
FIG. 2 illustrates a restriction endonuclease map of the fragment of plasmid QpRS.

Within the present invention, C. burnetii isolates were analyzed to determine how widely QpH1 plasmid sequences were distributed, and the extent to which they were conserved. Analyses of a large number (>30) of C. burnetii isolates demonstrated the stability of the QpH1 plasmid sequences in isolates obtained from around the world over a 40-year time span. The large majority of the isolates (>20) analyzed contained a plasmid which appeared to be identical to the QpH1 plasmid. However, isolates from three chronic endocarditis patients and two goat abortions shared a second plasmid type (designated QpRS) that was very similar to QpH1, as measured by hybridization and restriction enzyme analysis. Comparative restriction enzyme digests and mapping studies indicated that QpRS has unique regions, and is approximately 3 kilobase pairs (kbp) larger than QpH1 (FIG. 1). Analysis of three additional endocarditis isolates revealed that, although there was considerable homology of genomic DNA with QpRS and QpH1 plasmids, the restriction endonuclease digestion patterns of these three isolates were considerably different from those of QpRS and QpH1. An inability to isolate plasmids from this third group of C. burnetii suggested that plasmid sequences may have been integrated into the rickettsial chromosome. The present invention provides the first clear evidence that differences exist between C. burnetii isolates which cause distinguishable diseases.

In particular, the present invention provides superior methods for the rapid detection of C. burnetii, and additionally presents a method for predicting whether a particular C. burnetii infection will result in acute or chronic disease. The methods of the present invention do not require culture or serologic analysis of the biological sample, but rather utilize specific hybridization of a labeled DNA probe to DNA of cells obtained from a patient. If the patient's cells are infected with C. burnetii, the labeled DNA probe will hybridize to the rickettsial DNA and be subsequently detected A second labeled DNA probe, which selectively hybridizes to C. burnetii strains associated with chronic disease, is used for hybridization to DNA of cells suspected of containing these C. burnetii strains. Utilization of this differentiation technique allows a clinician to identify patients which might require specialized treatment or attention.

The methods for detection and differentiation of C. burnetii isolates are also applicable to epidemiological studies of both human and animal populations. The simplification and decreased expense provided by the diagnostic assay for C. burnetii described herein is also useful in the veterinary setting through eradication of infected animals from domestic livestock herds. Such eradication would be economically desirable to livestock owners, and would reduce or eliminate the animal reservoir responsible for human disease.

For many clinical specimens, detection of C. burnetii in biological samples may be optimized by concentration of the specimen. The concentrated specimen can then be immobilized onto a solid support to facilitate subsequent treatment, hybridization, and detection steps. Concentration, which may be accomplished by centrifugation, ensures that sufficient cellular material (containing the rickettsia) is immobilized to permit detectable DNA-DNA hybridization. A preferred solid support for immobilization is a DNA-binding filter membrane. In addition, hydroxyapatite columns or other DNA-binding materials may be used. The DNA-binding filter membrane manufactured by NEN Research, Boston, Mass., is particularly preferred.

In a preferred embodiment, the cells are treated prior to hybridization, so as to expose the cellular DNA before performing the DNA—DNA hybridization step. The cellular DNA may be exposed by a variety of techniques, which include lysing the cells or rendering the cells permeable. Subsequent treatment of the exposed cellular DNA, which generally includes immobilizing the DNA on a solid support, DNA denaturation, DNA neutralization, and heating under vacuum, is preferred. Prehybridization of the solid support after exposure of the cellular DNA and before DNA-DNA hybridization is also preferred.

As noted above, C. burnetii-specific DNA probes are labeled to facilitate detection of DNA-DNA hybridization. Preferred labels are radioisotopes and biotin. Radiolabels such as $^{32}P$, $^{3}H$, $^{32}S$ and $^{131}I$ are particularly preferred. Correspondingly, preferred hybridization detection systems are autoradiography and colorimetric assays, respectively.

To summarize the examples which follow, Example I describes methods for the rapid detection of C. burnetii DNA in a biological sample. Example II describes a method for differentiating C. burnetii strains that are capable of causing chronic disease from those that are capable of causing acute disease.

The following examples are offered by way of illustration and not by way of limitation.

EXAMPLE I

Detection of C. burnetii Growth and Purification

Rickettsia were propagated in the yolk sacs of embryonated White Leghorn eggs obtained from flocks fed an antibiotic-free diet. The embryonated eggs were inoculated at day 6 with appropriate stocks of C. burnetii diluted in 0.1% skim milk, incubated at 37° C., and candled daily. Eggs with dead embryos were discarded. The infected yolk sacs of viable embryos were harvested 8 days after inoculation with the agent, and the rickettsial organisms were partially purified as described by Hendricks and Mallavia (J. General Microbiol. 130:2857–2863, 1984). Thirty to sixty grams of yolk sacs was added to 100 ml of cold SP buffer (0.25M sucrose, 140 mM potassium chloride, 10 mM potassium phosphate, pH 7.2). The mixture was blended three times (30 seconds each) in a Sorvall (Dupont-Sorvall, Wilmington, Del.) homogenizer. The resultant homogenate was then centrifuged at 16,000 X g for 45 minutes in a refrigerated centrifuge. The supernatant and lipid layers were discarded, and the rickettsia-containing pellet was carefully resuspended in 100 ml cold SP buffer, using a 12-gauge cannula and syringe.

The mixture was centrifuged at 200 X g for 10 minutes, and the rickettsia-containing supernatant was centrifuged again at 21,000 X g for 45 minutes. The pellet was resuspended in 9 volumes of SP buffer and recentrifuged. The pellet was again resuspended in SP buffer and passed through an AP-20 filter to remove residual Celite and mitochondria. The filtrate was then centrifuged through a 30% sucrose-SP buffer clearing gradient; the pellet was resuspended and banded by isopyknic centrifugation in 30 to 60% linear sucrose gradients (Thompson et al., Biochem. J. 125: 365–366, 1971). The gradients were centrifuged at 100,000 X g for 120 minutes at 4° C. The rickettsial bands were harvested, diluted in SP buffer, and the dry weight of the organism was determined spectrophotometrically (Burton et al., J. Bacteriol. 122: 316–324, 1975). This was done by determining the Klett reading of organisms in solution and converting it to cell number, using a standard curve (Hackstadt, T. and J. C. Williams, J. Bacteriol. 148:419–425, 1981).

Preparation of DNA from Harvested Rickettsiae

Rickettsiae harvested from yolk sacs as described above were lysed by the addition of 100 ug/ml thermolysin and incubated for 60 minutes at room temperature; sodium dodecyl sulfate (SDS) was added to a final concentration of 1%(w/v). Thermolysin was used because of its broad proteolytic activity and absence of nuclease activity. Gentle but thorough mixing at room temperature for 10 to 20 additional minutes was required to effect complete lysis (Samuel et al., Infect. Immun. 41: 488–493, 1983). The crude DNA lysate can be used for plasmid isolation, or can be further purified by extraction with phenol/chloroform. The purified DNA is in the aqueous phase following phenol/chloroform extraction.

Isolation of Plasmid DNA

For plasmid isolation, the crude DNA lysate was mixed with CsCl (to a 4.5M final concentration) and ethidium bromide (~600 ug/ml). The resultant mixture was centrifuged to equilibrium (48 hours at 45,000 rpm in a Ti 60 [Beckman Instruments, Inc., Palo Alto, Calif.] rotor). The plasmid DNA/ethidium bromide complex, which bands at a density greater than that of chromosomal DNA, was visualized by fluorescence. The fluorescent DNA bands were located using long-wave ultraviolet light, and the individual bands were collected from the top, using a 12-gauge cannula and syringe. Standard extraction with chloroform, isoamyl alcohol, and ether was used to remove the ethidium bromide from each preparation (Maniatis et al., Molecular Cloning: A Laboratory Manual, Cold Spring Harbor Laboratory, Cold Spring Harbor, N.Y., 1982). The DNA samples were then extensively dialyzed against TE (10 mM Tris (pH 7.4), 1 mM EDTA) at 4° C. The resultant solution was adjusted to contain 250 mM sodium acetate, then precipitated overnight with 2 vol of 100% ethanol at −20° C. (Samuel et al., Infect. Immun. 41: 488–493, 1983). Plasmid DNA was pelleted by centrifugation at −20° C. for 45 minutes at 15,000 rpm in an SS34 rotor (Dupont-Sorvall). The DNA was washed with 70% ethanol, re-pelleted, and resuspended in TE (Currier and Nester, Anal. Biochem. 76:431–441, 1976).

Generation of Recombinant Plasmid pJSP1

QpH1 plasmid (FIG. 1) was obtained from the Nine Mile strain of C. burnetii (ATCC No. ATCVR-625), and purified using the procedure described above (Samuel et al., Infect. Immun. 41:488–493, 1983). Purified QpH1 DNA was digested with restriction endonuclease Pst I and electrophoresed in a preparative Tris-acetate-agarose gel (1.0%; Maniatis et al., Molecular Cloning: A Laboratory Manual, Cold Spring Harbor Laboratory, Cold Spring Harbor, N.Y., 1982).

To separate the various restriction fragments, electrophoresis was continued until the approximately 27 kbp piece was well separated from the 8.5-kbp fragment of QpH1. A well was cut in front of the 27 kbp plasmid, and a piece of dialysis tubing was placed in the well in a manner which blocked the entry of the DNA into the gel. The approximately 27 kbp DNA was then collected by electroelution into the well against the dialysis tubing, and the DNA was removed. This fragment of QpH1 was electrophoresed and extracted two times with phenol/chloroform. The resultant material was then ethanol precipitated. The pellet was resuspended in 200 ul $H_2O$ and 25 ul 3M sodium acetate, pH 5.2. The resultant solution was ethanol-precipitated, and the pellet rinsed in 10% ethanol and resuspended in TE. The 27-kbp fragment of QpH1 was ligated with pACYC 177 (Chang, A. C. Y. and S. N. Cohen, *J. Bacteriol.* 134:1141–1156, 1978), which had been digested to completion with Pst 1. Several vector-insert ratios were prepared, and a mixture of the best ligations, as determined by gel analysis, were used to transform *E. coli* RR1.

A number of different vectors could be used in this step. The inventors selected pACYC 177 because it was a nontransmissible derivative of p15A and transfers poorly, even in the presence of an F plasmid. The pACYC 177 plasmid vector is 3.7 kbp in size and contains both ampicillin and kanamycin resistance markers. This vector has a single Pst I cleavage site in the ampicillin resistance region, which allows the use of insertional inactivation as a method of detecting successful recombinant fragments. It should be noted that vectors containing a tetracycline resistance marker should not be used, since tetracyclines are the drugs of choice in the treatment of Q fever.

Following enzyme inactivation, the DNA was dephosphorylated with calf intestinal alkaline phosphatase (repurified; Sigma, St. Louis, Mo.). The pACYC 177 was combined with a 3M excess of the 27 kbp Pst I fragment of QpH1, and the mixture was ligated with $T_4$ DNA ligase (Maniatis et al., *Molecular Cloning: A Laboratory Manual*, Cold Spring Harbor Laboratory, Cold Spring Harbor, N.Y., 1982). This ligation mixture was transformed into *E. coli* RR1 using the standard calcium chloride transformation technique (Clewell, *J. Bacteriol.* 110:667–676, 1972). Single-colony isolates were selected and tested for the presence of QpH1 sequences using the method of Birnboim and Doly (*Nucl. Acid Res.* 7:1513–1523, 1979). The isolates obtained contained the sequences in either a 5'->3' orientation or a 3'->5' orientation. Either one will work as a probe. pJSP1 consists of the 5'->3' orientation (Mallavia et al., in: Microbiology, Amer. Soc. for Microbiol., Washington, D.C., pp. 293–296 (1984). The transformed bacteria were propagated, and single-colony isolates containing cloned QpH1 plasmid DNA were selected by insertional inactivation of antibiotic resistance ($Kan^r$ and $Amp^s$).

Figure 3:
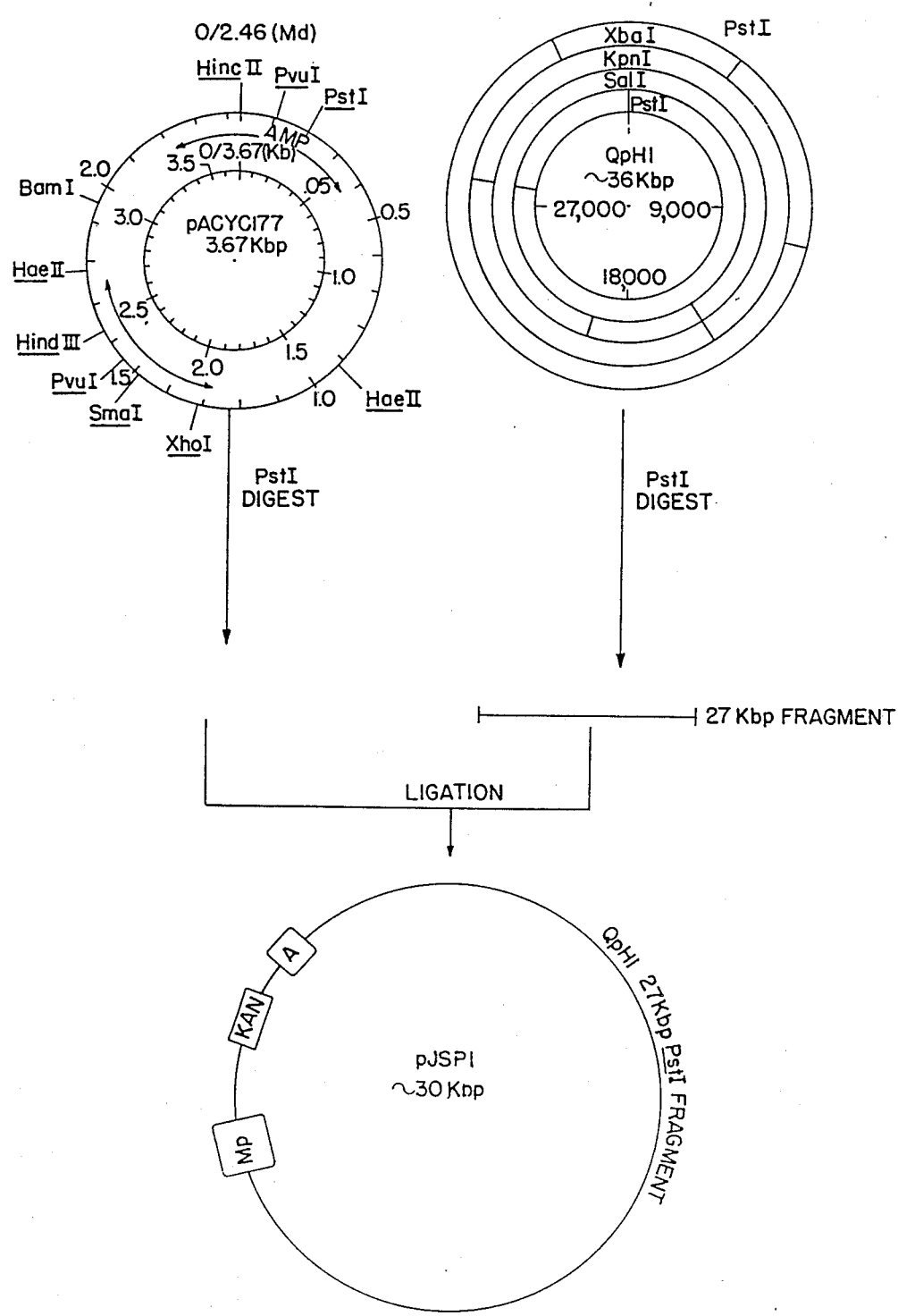
FIG. 3 illustrates the construction of recombinant plasmid pJPS1.

Following amplification in *E. coli* RR1, the structure of the plasmid was verified by restriction mapping and Southern techniques (Southern, E. J., *Molec. Biol.* 98: 503–517, 1975). The structure of the resultant recombinant plasmid, pJSP1, was shown in FIG. 3. This construct was used to produce a labeled DNA probe for detecting the presence of *C. burnetii* in biological samples.

Purified pJS1 DNA was digested to completion with Pst I and electrophoresed in a preparative Tris acetate agarose gel. The 27 kbp restriction fragment was separated from the ~3.7 kpb of pACYC 177 and the 27 kbp fragment was collected using the same method described earlier in this section. The QpH1-derived 27 kpb probe was nick-translated using either $^{32}P$- (Maniatis and Klein, *Proc. Natl. Acad. Sci.* 72: 1184–1188, 1975) or biotin-labeled (Leary et al., *Proc. Natl. Acad. Sci.* 80:4045–4049, 1983) nucleotides. The labeled DNA probe was hybridized to cellular DNA, which had been immobilized on a DNA-binding filter membrane (NEN Research, Boston, Mass.), using either Southern (Southern, E. J., *Molec. Biol.* 98:503–517, 1975) or dot blot hybridization protocols.

Assay for Detection of *C. burnetii*

Ten to twenty ml of whole blood was centrifuged to concentrate the white blood cells, which was used as a "buffy coat". The "buffy coat" was placed on a two-step gradient of 5 ml of 40% Ficoll-Hypaque ® (Winthrop Laboratories, Sterling Drug, Inc., New York, N.Y.) on top of 5 ml of 60% Ficoll-Hypaque, both diluted in phosphate-buffered saline (PBS). White cells were isolated from the 40–60% interface, washed in PBS, and resuspended in a small volume (~20 ul) of PBS. The purified white blood cells, and the rickettsial cells contained within them, were absorbed on a DNA-binding filter membrane (NEN Research). These membranes were then treated by being placed sequentially on 3MM Whatman paper soaked with an appropriate solution. Cells were first lysed with a solution of 0.2%(w/v) SDS/0.5M NaOH/1.5M NaCl. The rickettsial DNA was then denatured with 0.5M NaOH/1.5M NaCl, and neutralized with a solution of 0.5M Tris —HCl (pH 7.5)/1.5M NaCl. Each treatment was carried out for 15 minutes. The membrane was heat-treated under vacuum at 80° C. for 2 hours, then prepared for hybridization.

Prior to hybridization, the membrane was prehybridized with a solution of 50%(v/v) deionized formamide, 0.75M NaCl, 0.075M sodium citrate, 20 mM Tris -HCl (pH 8.0), 1 mM EDTA, and 20 ug/ml denatured salmon sperm DNA. Hybridization was then carried out by the addition of >5 ng/ml of a heat-denatured, high specific activity, nick-translated *C. burnetii*-specific DNA probe (pJSP1), which was previously described. Hybridization was performed at 42° C. for 20 to 24 hours. Non-hybridized, labeled DNA probe was then removed by washing the filter in 0.1X SSC (20X SSC consists of 175.3 g NaCl and 88.2 g of sodium citrate/liter, pH 7.0), 0.1%(w/v) SDS, and 5 mM EDTA.

Hybridized, radiolabeled, *C. burnetii*-specific DNA probe was detected by autoradiography. Hybridized, biotinylated *C. burnetii*-specific DNA probe was detected by an avidin-biotin enzyme-activated (alkaline phosphatase or horseradish peroxidase) colorimetric detection system.

As a simplified alternative to the assay for detecting *C. burnetii* set forth above, whole blood was diluted with an equal volume of physiological saline. The blood (up to 8 ml), was then layered onto 3 ml of Ficoll-Paque (Pharmacia, Piscataway, N.J.) and centrifuged for 10 minutes at 2300 rpm in a Beckman TJ6 centrifuge at room temperature. The white cell layer was removed, and washed by centrifugation for 15 minutes at 2300 rpm at 4° C. in physiological saline. The resultant cell pellet was resuspended in saline G and deposited onto BA85 nitrocellulose filters (Millipore Corporation, Bedford, Ma.) using a dot blot, slot blot, or other filtration apparatus. To these cells, 5 ml of lysing solution (1% SDS, 10 mM EDTA, 10 mM Tris, pH 7.5, 150 mM NaCl, and 50 ug/ml) proteinase K preheated to 60° C.)

was added. The cells were allowed to sit in this solution for 15 minutes. After lysis, the cells were rinsed twice (5 ml each) with saline. DNA was treated with 5 ml denaturing solution (1.5M NaCl and 0.5M NaOH); after 15 minutes, this solution was removed by filtration and 5 ml of neutralizing solution (1M Tris HCl, pH 7.0, 1M NaCL) was added and allowed to set for 5 minutes at room temperature. Following filtration of neutralizing solution, the filter-bound DNA was washed twice with 2X SSC. The filters were then dried under vacuum at 80° C. for 2 hours and prepared for hybridization. Hybridizations were carried out as previously described, with the exception that the final wash used 1X SSC. The higher stringency or homology provided by these conditions decreased any likelihood of false positives in either the detection of *C. burnetii* or in the differentiation between chronic and acute strains.

Detection of *C. burnetii* Using Blood Samples

Using the simplified assay system set forth above, *C. burnetii* has been detected in blood (1 ml), from guinea pigs infected 4–5 days earlier. Using $^{32}$P-labeled probe (specific activity $5 \times 10^5$ cpm/ml) in controlled experiments, one can detect $10^4$ *Coxiella burnetii* cells. DNA from a million WBC had no effect on the hybridization signal from rickettsial DNA. Differential diagnosis between rickettsial strains required $10^5$ organisms under these conditions because of the smaller probe size. However, it will be evident to those skilled in the art that probes of higher specific activity as well as signal-intensifying techniques may be utilized in order to increase sensitivity (and, therefore, decrease the numbers of rickettsia required) by at least an order of magnitude.

Detection of *C. burnetii* Using Urine Samples

It is also possible to detect the presence of *C. burnetti* in urine. It is important to note that the concentrations of rickettsia in urine [$10^2$–$10^3$ guinea pig infectious doses/ml (GPID)] are much lower than are observed in blood ($10^4$–$10^6$ GPID/ml). In this assay, the urine can be either centrifuged to pellet the organisms or filtered directly through the nitrocellulose filter. Subsequently the cells are treated with lysing solution, rinsed, and the DNA treated as set forth above in the simplified assay procedure.

EXAMPLE II

Differentiation of *C. burnetii* Strains

The QpRS plasmid was obtained from the Priscilla Q177 strain of *C. burnetii* which is available from either Rocky Mountain Laboratories, National Institute of Allergy and Infectious Diseases, Hamilton, Mont., or from Dr. L. P. Mallavia, Dept. of Microbiology, Washington State University, Pullman, Wash. who has the same on deposit in his laboratory. The Priscilla Q177 strain of *C. burnetii* was grown and purified in the same manner described in Example I, and QpRS plasmid DNA was obtained by using the purification scheme outlined for QpH1.

*C. burnetii* plasmid QpRS contains unique DNA sequences which are not present in plasmid QpH1 and these unique sequences have been associated with *C. burnetii* strains that have the capacity to cause chronic disease. These unique QpRS sequences have been utilized in a second radiolabeled DNA probe, which can be used to differentiate *C. burnetii* isolates likely to cause chronic illness from those likely to cause acute Q fever.

Generation of Recombinant Plasmid pOB1

Figure 4:
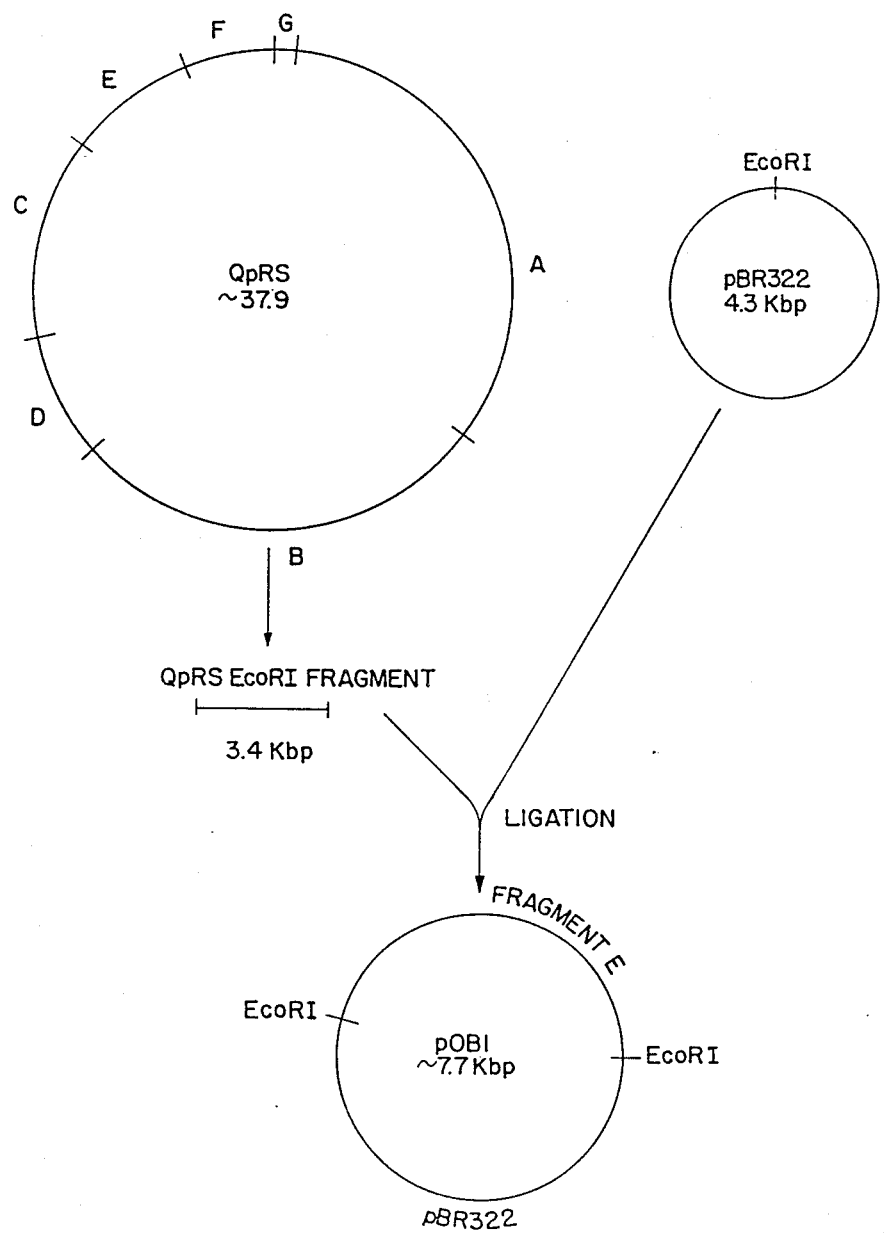
FIG. 4 illustrates the construction of recombinant plasmid pOB1.

The 3.4–3.6 kbp Eco RI fragment of plasmid QpRS (designated QpRS Eco RI fragment E) was cloned into the Eco RI site of plasmid pBR322 to produce the recombinant plasmid pOB1 (FIG. 4). Plasmid pBR322 was fully cleaved with Eco RI; and following enzyme inactivation, the DNA was dephosphorylated with calf intestine alkaline phosphatase (repurified; Sigma, St. Louis, Mo.). The pBR322 DNA was combined with a 3M excess of the ~3.4-kbp QpRS Eco RI fragment E, and the mixture was ligated with T$_4$ DNA ligase (Maniatis et al., *Molecular Cloning: A Laboratory Manual*, Cold Spring Harbor Laboratory, Cold Spring Harbor, N.Y., 1982). This ligation mixture was transformed into *E. coli* HB101, using the standard calcium chloride transformation technique (Clewell, *J. Bacteriol.* 110:667–676, 1972). Single-colony isolates were selected and tested for the presence of QpRS-specific sequences, using the method of Birnboim and Doly (*Nucl. Acid Res.* 7:1513–1523, 1979).

The pOB1 recombinant plasmid was amplified and used to produce a labeled DNA probe that can differentiate *C. burnetii* strains capable of causing hepatitis, chronic endocarditis and other chronic infections from those capable of causing acute Q fever.

Assay for Differentiation

The QpRS-derived probe, which recognizes *C. burnetii* DNA that is associated with chronic disease, was prepared by isolating and purifying pOB1. The plasmid DNA was digested to completion with Eco RI and electrophoresed to separate pBR322 sequence from the ~3.4 kbp QpRS Eco RI fragment E. The ~3.4 kbp fragment was collected using the procedure outlined for QpH1 and nick-translated with $^{32}$P- or biotin-labeled nucleotides, as described above. While the whole 3.4–3.6 kbp fragment of plasmid QpRS can be used for differential diagnosis, a portion of this fragment has sequence homology to the QpH1 plasmid and will therefore cross react at low stringencies. In order to eliminate any chance of cross reactivity, the large Xba Eco RI fragment (2.4 Kbp) can be used as a probe. Cells suspected of containing *C. burnetii* were concentrated from biological samples and immobilized on a DNA-binding filter membrane (NEN Research). The cellular DNA was treated and prehybridized, as previously described. The cellular DNA was then hybridized with a labeled, QpRS- derived DNA probe. Hybridization and detection of the labeled DNA probe was performed as described above, thereby allowing the detection of strains of *C. burnetii* associated with chronic disease.

The assay described above may be utilized in conjunction with the detection assays previously described, in order to differentiate strains of *C. burnetii* that are capable of causing acute disease from those strains capable of causing chronic disease. Samples that hybridize with the QpH1-derived probe, but not with the QpRS-derived probe, indicate *C. burnetii* infection associated with acute disease. Samples that hybridize with both the QpH1 and QpRS-derived probes indicate *C. burnetii* infection capable of causing chronic disease.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for differentiating strains of *C. burnetii* that are capable of causing acute disease from those strains capable of causing chronic disease, comprising:

treating cells contained within a biological sample and suspected of containing *C. burnetii* to expose cellular DNA;

hybridizing a first aliquot of the cellular DNA with a DNA probe which specifically hybridizes with *C. burnetii* DNA;

hybridizing a second aliquot of the cellular DNA with a labeled DNA probe derived from the Xba-Eco RI portion of fragment E of plasmid QpRS and containing DNA sequences that specifically hybridize with *C. burnetii* DAN of strains associated with the capacity of cause chronic disease; and detecting the hybridized, labeled DNA probes, and therefrom differentiating the strain of *C. burnetii*.

2. The method of claim 1 including, prior to the step of treating, immobilizing the cells onto a solid support.

3. The method of claim 2 including, after the step of immobilizing, prehybridizing the DNA immobilized on the solid support.

4. The method of claim 1 including, prior to the step of treating, concentrating the cells contained within the biological sample.

5. The method of claim 1 wherein the DNA probe which specifically hybridizes with *C. burnetii* DNA in the first aliquot is derived from a plasmid isolated from the Nine Mile strain of *C. burnetii*.

6. The method of claim 1 wherein the plasmid QpRS is isolated from the Priscilla strain of *C. burnetii*.

* * * * *

UNITED STATES PATENT AND TRADEMARK OFFICE
CERTIFICATE OF CORRECTION

PATENT NO. : 4,895,795

DATED : January 23, 1990

INVENTOR(S) : Marvin E. Frazier et al.

It is certified that error appears in the above-identified patent and that said Letters Patent is hereby corrected as shown below:

In claim 1, column 12, line 1, delete "DAN" and substitute therefor --DNA--, line 2, delete "of" and substitute therefor --to--.

Signed and Sealed this

Ninth Day of July, 1991

Attest:

Attesting Officer

HARRY F. MANBECK, JR.

Commissioner of Patents and Trademarks